(12) United States Patent
Metzler et al.

(10) Patent No.: US 9,908,894 B2
(45) Date of Patent: Mar. 6, 2018

(54) METHODS FOR THE PREPARATION OF 1,3-BENZODIOXOLE HETEROCYCLIC COMPOUNDS

(71) Applicant: Leo Pharma A/S, Ballerup (DK)

(72) Inventors: Bjorn Metzler, Ballerup (DK); Andre Faldt, Ballerup (DK)

(73) Assignee: LEO Pharma A/S, Ballerup (DK)

( * ) Notice: Subject to any disclaimer, the term of this patent is extended or adjusted under 35 U.S.C. 154(b) by 0 days.

(21) Appl. No.: 15/320,227

(22) PCT Filed: Jun. 22, 2015

(86) PCT No.: PCT/EP2015/063942
§ 371 (c)(1),
(2) Date: Dec. 19, 2016

(87) PCT Pub. No.: WO2015/197534
PCT Pub. Date: Dec. 30, 2015

(65) Prior Publication Data
US 2017/0137438 A1    May 18, 2017

(30) Foreign Application Priority Data
Jun. 23, 2014 (EP) .................... 14173397

(51) Int. Cl.
*C07D 495/10* (2006.01)

(52) U.S. Cl.
CPC .................. *C07D 495/10* (2013.01)

(58) Field of Classification Search
CPC .................... C07D 495/10
USPC .......................... 546/15
See application file for complete search history.

(56) References Cited

U.S. PATENT DOCUMENTS

| | | | | |
|---|---|---|---|---|
| 6,716,987 B1 * | 4/2004 | Ohshima | ............... | C07D 307/79 544/106 |
| 8,338,431 B2 * | 12/2012 | Bollu | .................. | C07D 491/10 514/255.05 |
| 8,980,905 B2 * | 3/2015 | Nielsen | ................ | C07D 493/10 514/278 |
| 9,273,064 B2 * | 3/2016 | Nielsen | ................ | C07D 493/10 |
| 9,637,499 B2 * | 5/2017 | Nielsen | ................ | C07D 493/10 |
| 2003/0203918 A1 * | 10/2003 | Meade | ................... | A61K 31/36 514/254.11 |
| 2005/0245750 A1 * | 11/2005 | Atsumi | ................ | A61K 31/357 549/341 |
| 2008/0015226 A1 * | 1/2008 | Amari | .................. | C07D 213/61 514/318 |
| 2010/0035908 A1 * | 2/2010 | Felding | ................ | C07D 213/61 514/277 |
| 2010/0099688 A1 * | 4/2010 | Felding | ................ | C07D 491/10 514/255.05 |
| 2013/0123291 A1 * | 5/2013 | Nielson | ................ | C07D 493/10 514/278 |
| 2015/0111915 A1 * | 4/2015 | Nielsen | ................ | C07D 493/10 514/278 |
| 2016/0022657 A1 * | 1/2016 | Nielsen | ................ | C07D 493/10 514/278 |

FOREIGN PATENT DOCUMENTS

| | | |
|---|---|---|
| WO | 2008/077404 | 7/2008 |
| WO | 2008/104175 | 9/2008 |
| WO | 2011/160632 | 12/2011 |
| WO | WO2014096018 | * 6/2014 |
| WO | WO2017103058 | * 6/2017 |

OTHER PUBLICATIONS

Yanagisawa; Org. Process Res. Dev. 2011, 15, 376-381.*
International Search Report and Written Opinion of ISA/EP dated Jan. 26, 2016, for PCT/EP2015/063942.

* cited by examiner

*Primary Examiner* — Daniel R Carcanague
(74) *Attorney, Agent, or Firm* — Fish & Richardson P.C.

(57) ABSTRACT

The present invention relates to novel methods for the preparation of 1,3-benzodioxole heterocyclic compounds and intermediates for the same. The compounds are useful as PDE4 inhibitors.

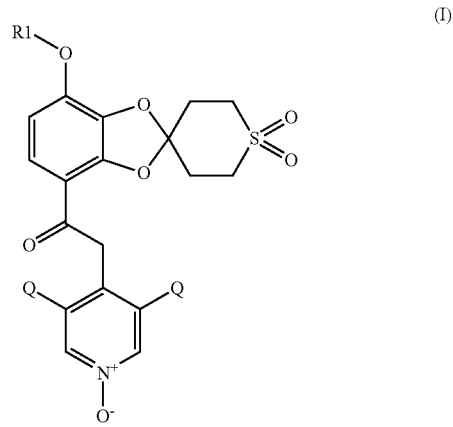

9 Claims, No Drawings

METHODS FOR THE PREPARATION OF 1,3-BENZODIOXOLE HETEROCYCLIC COMPOUNDS

FIELD OF THE INVENTION

The present invention relates to novel methods for the preparation of 1,3-benzodioxole heterocyclic compounds and intermediates for the same. The compounds are useful as PDE4 inhibitors.

BACKGROUND OF THE INVENTION

WO 2011/160632 discloses benzodioxole and benzodioxepene heterocyclic compounds useful as PDE4 inhibitors as well as suitable methods for the preparation thereof.

WO 2008/104175 discloses benzodioxole and benzodioxepene heterocyclic compounds useful as PDE4 inhibitors as well as suitable methods for the preparation thereof.

WO 2008/077404 discloses substituted acetophenones useful as PDE4 inhibitors as well as suitable methods for the preparation thereof.

In the development of new drug candidates, it is highly desirable to have access to alternative methods for the preparation of the drug candidates, as some efficient small-scale synthesis may turn out to be difficult to up-scale to production scale quantities. Also, small-scale syntheses may involve reagents and solvents which are not feasible to utilize at a production scale level.

Hence, it is an object of the present invention to provide alternative methods for the preparation of 1,3-benzodioxole heterocyclic compounds of the type disclosed in WO 2011/160632, insofar that such alternative methods provide advantages with respect to one or more features like the number of reactions steps, purity, yield, ease of purification, process economy, availability of starting materials and reagents, safety, predictability, etc.

SUMMARY OF THE INVENTION

It has been found by the present inventors that the alternative method disclosed herein provides advantages over the known methods by a reduced number of reactions steps, from the previous 10 steps to now 4 steps, by reducing work load regarding synthesis of substance, an improved overall chemical- and volumetric yield and ease of the production method as some intermediates are not isolated.

Hence, the present invention provides a method for the preparation of 1,3-benzodioxole compounds, e.g. a compound of formula (I).

Also within the scope of the invention are intermediates used in the foregoing method for preparing compounds of formula (I), and methods of making such intermediates comprising one or more of the foregoing steps as indicated.

DETAILED DISCLOSURE OF THE INVENTION

In a first aspect, the present invention relates to a method for the preparation of a compound of formula (I)

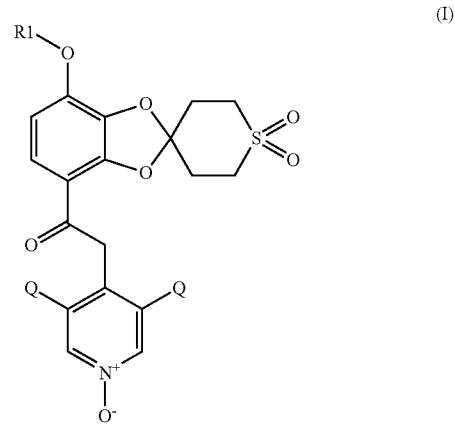

(I)

wherein $R_1$ is selected from $CHF_2$ and $CF_3$, and Q is selected from chloro, bromo and fluoro.

In the compound of formula (I), $R_1$ is typically $CHF_2$. Q is typically selected from chloro, bromo and fluoro, preferably chloro, where the Q's preferably are the same. In one embodiment, both Q's are chloro.

Definitions

The term "$C_{1-6}$-alkyl" is intended to mean a saturated, straight or branched hydrocarbon chain having from one to six carbon atoms, including methyl, ethyl, propyl, isopropyl, butyl, isobutyl, secondary butyl, tertiary butyl, pentyl, isopentyl, neopentyl, tertiary pentyl, hexyl and isohexyl. In some embodiments, "$C_{1-6}$-alkyl" is a $C_{1-4}$-alkyl group, e.g. methyl, ethyl, propyl, isopropyl, butyl, isobutyl, secondary butyl and tertiary butyl. Correspondingly, "$C_{1-3}$-alkyl" includes methyl, ethyl, propyl and isopropyl.

The term "halogen" is intended to mean one of fluoro, chloro, bromo and iodo. In one embodiment, the term "halogen" designates fluoro or chloro. In another embodiment, the term "halogen" designates chloro.

The term "aryl" is intended to mean a carbocyclic aromatic ring system derived from an aromatic hydrocarbon by removal of a hydrogen atom. Aryl furthermore includes bi-, tri- and polycyclic ring systems. Examples of preferred aryl moieties include phenyl, naphthyl, indenyl, indanyl, fluorenyl, and biphenyl. Preferred "aryl" is phenyl, naphthyl or indanyl, in particular phenyl, unless otherwise stated.

The term "arylalkyl" is intended to mean an aryl radical as defined above covalently joined to an alkyl group, e.g. benzyl.

Methods of Preparation

It appears that the method provides advantages over the known methods by relying on cheap starting materials, and ease of the production method as some intermediates are not isolated and the reduced number of reaction steps. Also, the overall yield has been improved by a factor of 2.5.

Step (1)

The method for the preparation of a compound of the formula (I) includes the formation of a compound of the formula (IV) which is obtained by reacting a compound of formula (II)

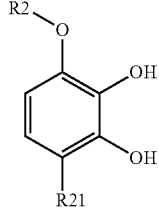
(II)

wherein $R_2$ is selected from hydrogen, $C_{1-6}$-alkyl and arylalkyl, $R_{21}$ is selected from hydrogen, $C(O)R_{22}$ and $C(O)OR_{22}$, and $R_{22}$ is selected from hydrogen and $C_{1-6}$-alkyl; with a compound of formula (III)

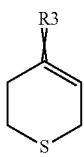
(III)

wherein "⋊⋉" represents a single bond, a double bond or two single bonds, and when "⋊⋉" represents a double bond or two single bonds, "=" is a single bond, and when "⋊⋉" represents a single bond, "=" is a double bond, $R_3$ represents oxygen when "⋊⋉" represents a double bond and $R_3$ represents O—$C_{1-6}$-alkyl when "⋊⋉" represents a single bond or two single bonds; in the presence of an acid catalyst to form a compound of formula (IV)

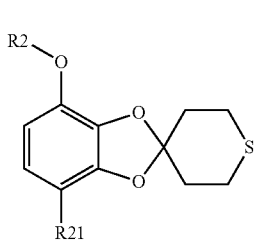
(IV)

wherein $R_2$ and $R_{21}$ is as defined above.

The acid catalyst is typically in form of a silicate mineral. The silicate mineral is typically selected from Montmorillonite K10, Montmorillonite K30, Montmorillonite KSF, Zeolite HSZ-341NHA, Zeolite HSZ-331NHA, Zeolite HSZ-350HUA and Zeolite HSZ-360HUA. In one embodiment, the silicate mineral is selected from Montmorillonite K10 and Zeolite HSZ-360HUA. In another embodiment, the silicate mineral is Montmorillonite K10.

The compound of formula (III) is typically selected from

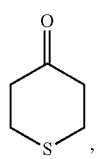
(IIIa)

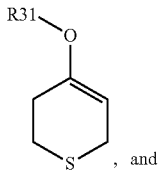
(IIIb)
, and

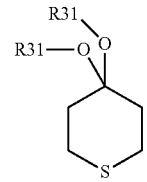
(IIIc)

wherein $R_{31}$ represents $C_{1-6}$-alkyl. In one embodiment, the compound of formula (III) is selected from the compounds of formula (IIIa), and formula (IIIb), wherein $R_{31}$ represents methyl.

The ratio between the silicate mineral and compound of formula (II) may have influence on the filtration-time. Hence, it is typically preferred to have an amount of the mineral of 25%-w/w to 500%-w/w compared to the compound of formula (II). In particular the amount of mineral should be of at least 50%-w/w to 200%-w/w.

The reaction is typically conducted in toluene, benzene, 2-Methyl-THF (2-methyl-tetrahydrofuran), EtOAc (ethyl acetate), xylenes, heptane, octane, chlorobenzene and dichlorbenzene. In one embodiment, the solvent is toluene.

The reaction is typically conducted at a temperature above 80° C. in order to promote the reaction. Hence, it is typically preferred that the temperature is in the range of 80-200° C., such as in the range of 100-160° C., especially at 110° C. The reaction is typically allowed to proceed for 4-96 hours, such as 24-72 hours.

The resulting compound of formula (IV) may be recovered by conventional means, known to those skilled in the art, e.g. by filtration.

In one embodiment of the invention, the compound of formula (II) is wherein $R_2$ is selected from hydrogen or methyl and $R_{21}$ is selected from hydrogen, $COCH_3$ or COOH. In another embodiment, the compound of formula (II) is 2,3-dihydroxy-4-methoxyacetophenone.

In one embodiment of the invention, the compound of formula (III) is tetrahydro-4H-thiopyran-4-one.

In one embodiment of the invention, the compound of formula (IV) is wherein $R_2$ is hydrogen, methyl, ethyl, propyl, isopropyl, isobutyl, secondary butyl, tertiary butyl or benzyl, and $R_{21}$ is selected from hydrogen, $COCH_3$ or COOH. In another embodiment the compound of formula (IV) is wherein $R_2$ is methyl and $R_{21}$ is $COCH_3$.

Steps (2a) and (2b)

The reaction steps (2a) and (2b) are performed as a one-pot reaction indicating that the intermediate compound (VI) is not isolated.

In step (2a), the enolate compound of formula (IV) is reacted with a pyridine compound of formula (V)

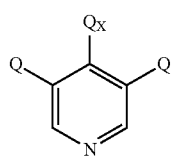

wherein Q is as defined above and $Q_x$ is selected from chloro, bromo, fluoro and iodo to form an intermediate compound of formula (VI)

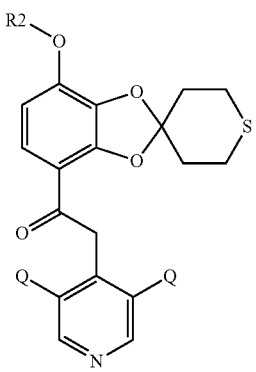

wherein $R_2$ and Q are as defined above; followed by deprotecting in step (2b), where the intermediate compound of formula (VI) is reacted with a compound of formula (VII)

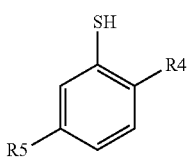

wherein $R_4$ and $R_5$ independently represent $C_{1-6}$-alkyl, to form a compound of formula (VIII)

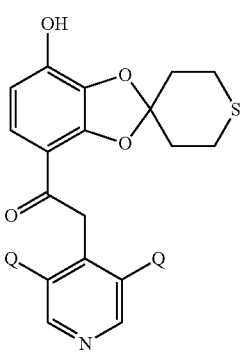

wherein Q is defined above.

The pyridine coupling, step (2a), is typically conducted in an aprotic polar solvent, e.g. selected from NMP (N-methylpyrrolidone), DMF (N,N-dimethylformamide), DMI (1,3-dimethyl-2-imidazolidinone), DMSO (dimethyl sulfoxide), EtOAc (ethyl acetate), MeCN (acetonitrile) and THF (tetrahydrofuran), and mixtures hereof, in the presence of a base, e.g. selected from tert-BuONa (sodium tert-butoxide), tert-BuOK (potassium tert-butoxide), tert-BuOLi (lithium tert-butoxide) $K_2CO_3$, $Na_2CO_3$, $KHCO_3$, $NaHCO_3$, $Et_3N$ (triethylamine) and DIPEA (N,N-diisopropylethylamine). In one embodiment, the aprotic solvent is selected from DMF and NMP, in the presence of tert-BuONa as the base. In a particular embodiment, the aprotic solvent is NMP and the base is tert-BuONa.

The base is usually used in approximately stoichiometric amounts relative to the compound of the formula (V), such as where the equivalent ratio (base)/(formula V) is from 1:1 to 3:1, e.g. from 1.5:1 to 2:1, especially from 1.7:1 to 1.9:1.

The reaction (2a) is typically conducted at a temperature above 0° C. and below 15-20° C., such as in the range of 5-10° C.

In one embodiment of the invention, the compound of formula (V) is 3,4,5-trichloropyridine.

The deprotection of the alkyl group in step (2b) may be conducted using various solvents, e.g. selected from NMP (N-methylpyrrolidone), DMSO (dimethyl sulfoxide), DMF (N,N-dimethylformamide), and mixtures hereof, in the presence of a base, e.g. selected from $K_2CO_3$, $Na_2CO_3$, $KHCO_3$, $NaHCO_3$, $CsCO_3$, TEA (triethanolamine), tert-BuOLi (lithium tert-butoxide) and DIPEA (N,N-diisopropylethylamine). In one embodiment, the solvent is selected from NMP, DMSO and DMF, in the presence of $K_2CO_3$ as the base. In another embodiment, the solvent is NMP and the base is $K_2CO_3$.

The reaction is typically conducted at a temperature in the range of 50-120° C., such as in the range of 70-100° C. The reaction is typically allowed to proceed for 2-36 hours, such as 5-24 hours.

Various reagents of formula (VII) may be used. In one embodiment of the invention, the compound of formula (VII) is wherein $R_4$ and $R_5$ independently are selected from methyl tertiary butyl. In another embodiment the compound of formula (VII) is 5-tert-butyl-2-methyl thiophenol.

The resulting compound of formula (VIII) may be recovered by conventional means, known to those skilled in the art, e.g. by aqueous workup followed by extraction and finally precipitation and filtration.

In one embodiment of the invention, the compound of formula (VIII) is wherein Q is selected from chloro, bromo and fluoro. In another embodiment the compound of formula (VIII) is wherein Q is chloro.

Step (2c)

In step (2c) the compound of formula (VIII) is reacted with aqueous $N(Bu_4)^+OH^-$ to form a compound of formula (IX)

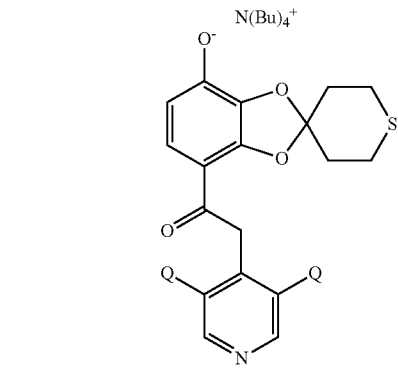

wherein Q is as defined above.

The crude compound of formula (VIII) may be dissolved, e.g. in THF, toluene or EtOAc before the addition of aqueous N(Bu₄)⁺OH⁻. In one embodiment of the invention, the crude compound of formula (VIII) is dissolved THF.

The resulting mixture is typically heated to a temperature in the range of 20-60° C., such as 45° C., and the reaction is typically allowed to proceed for 0.5-5 hours, such as 1-2 hours ensuring the salt formation.

The resulting product is typically obtained by precipitation by first suspending the crude product of formula (IX) in MTBE (methyl-tert-butylether) or heptane, water and a salt (NaCl) for 1-2 hours; subsequently cooling of the mixture to 0-20° C., e.g. 5° C. over a period of 1-24 hours, such as 1-4 hours causing the TBA (tetrabutylammonium) salt to precipitate.

Step (3)

The compound of formula (XI)

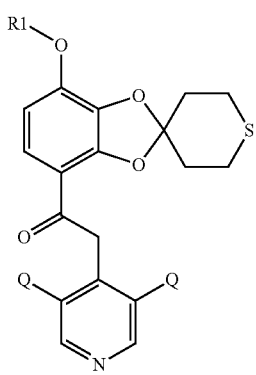

(XI)

wherein $R_1$ and Q are as defined above, may be obtained by alkylating the resulting compound of formula (IX) by reacting with a hydrochlorofluorocarbon reagent, $R_1$—Cl, wherein $R_1$ is as defined above.

The alkylation may be conducted using one of various possible reagents, such as various hydrochlorofluorocarbon gases under pressure. In one embodiment, the alkylation reaction is conducted using chlorodifluoromethane in an aprotic polar solvent, e.g. selected from DMF (N,N-dimethylformamide), NMP (N-methylpyrrolidone), DMI (1,3-dimethyl-2-imidazolidinone), DMSO (dimethyl sulfoxide), EtOAc (ethyl acetate), MeCN (acetonitrile) and THF (tetrahydrofuran), and mixtures hereof. In one preferred embodiment, the aprotic solvent is selected from DMF and NMP. In a particular embodiment, the reaction is conducted using chlorodifluoromethane in DMF.

The reaction is typically conducted at a temperature in the range of 40-120° C., such as in the range of 50-70° C. The reaction is typically allowed to proceed until completion.

The resulting compound of formula (XI) may be recovered by conventional means, known to those skilled in the art, e.g. by aqueous workup followed by precipitation and subsequently filtration.

Step (4)

The oxidation of the resulting compound of formula (XI) is conducted to form the compound of formula (I)

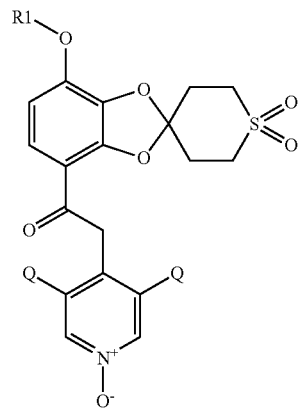

(I)

wherein $R_1$ and Q are as defined above, by reacting said compound of formula (XI) with an oxidation reagent.

The oxidation reagent is typically selected from PAA (peracetic acid) in AcOH (acetic acid), and $H_2O_2$ (aq) in formic acid or acetic acid. In one preferred embodiment, the oxidation reagent is PAA in AcOH. In one embodiment the amount of PM used relative to (I) is typically 3 to 6, especially 4 eq. The oxidation reagent is typically slowly added over a period of 1-8 hours, such as 3-5 hours, keeping the temperature in the range of 20-100° C., such as in the range of 25-50° C., especially in the range of 25-40° C.

The reaction is typically conducted at a temperature in the range of 30-70° C., such as 35-45° C., and stirred for 3-24 hours, such as 14-18 hours.

Purification of the Compound of Formula (I)

The resulting crude product of formula (I) may advantageously be purified by crystallization, precipitation, chromatography or the like.

In one embodiment the resulting crude product of formula (I) is crystallized from a mixture of water and EtOH (ethanol), and isolated by filtration and dried.

The Intermediates

In another aspect, the present invention relates to intermediates which are useful in the preparations of a compound of the formula (I) wherein $R_1$ is selected from $CHF_2$ and $CF_3$, and Q is selected from chloro, bromo and fluoro.

In one embodiment the invention relates to the intermediate compound of formula (IV)

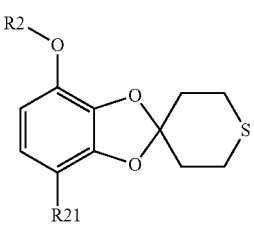

(IV)

wherein $R_2$ is selected from hydrogen, $C_{1-6}$-alkyl and arylalkyl, $R_{21}$ is selected from hydrogen, $C(O)R_{22}$ and $C(O)OR_{22}$, and $R_{22}$ is selected from hydrogen and $C_{1-6}$-alkyl. In another embodiment $R_2$ represents hydrogen, methyl, ethyl, propyl, isopropyl, isobutyl, secondary butyl, tertiary butyl or benzyl, and $R_{21}$ is selected from hydrogen, $COCH_3$ or COOH. In another embodiment, the intermediate compound of formula (IV) is 1-(7-methoxyspiro[1,3-benzodioxole-2,4'-tetrahydrothiopyran]-4-yl)ethanone.

In another embodiment the invention relates to a compound of formula (IX)

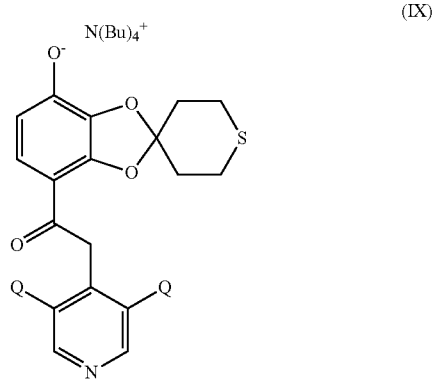

(IX)

wherein Q is selected from chloro, bromo and fluoro, preferably chloro, where the Q's preferably are the same. In one embodiment, both Q's are chloro. In another embodiment, the intermediate compound of formula (IX) is 2-(3,5-dichloropyridine-4-yl)-1-(7-tetrabutylamminium oxido-2',3',5',6'-tetrahydro-spiro[1,3-benzodioxole-2,4'-(4H)-thiopyran]-4-yl)ethanone.

EXPERIMENTALS

Methods and Reagents

All chemicals and reagents used are available i.a. from Sigma Aldrich Chemicals.

HPLC:

| Column | Sample | Flow (ml/min) | Detector | Mobile phase (% vol./vol.) |
|---|---|---|---|---|
| Aeris Peptide 3.6 μm, XB-C18 | 10 μl/5 mg sample in 5 ml eluent | 1.2 | 220 nm | Isocratic: 60% H$_2$O, 40% ACN, 0.1% TFA |

Example 1

Step (1): Preparation of 1-(7-methoxyspiro[1,3-benzodioxole-2,4'-tetrahydrothiopyran]-4-yl)ethanone A reactor was charged with 2,3-dihydroxy-4-methoxyacetophenone (1.0 kg, 5.49 mol), tetrahydro-4H-thiopyran-4-one (0.62 kg, 5.34 mot) and Montmorillonite K10 (0.5 kg) followed by addition of toluene (12 L). The suspension was heated to reflux by applying 150° C. at the reactor-mantle while the condenser was equipped with a Dean-Stark type equipment to allow for removal of the water formed by the reaction. The reflux was maintained for another 24 to 72 hours or until an in-process control showed >25% conversion (based on the ratio between 2,3-dihydroxy-4-methoxyacetophenone and the title compound %-area on HPLC). Un-reacted 2,3-dihydroxy-4-methoxyacetophenone was recovered by hot filtration (removing the K10) of the reaction mixture, washing three times of the filter-cake by hot toluene (2 L each) and one washing with hot EtOAc (1 L).

The combined warm filtrates were cooled to 5° C. during 2 to 3 hours causing the un-reacted 2,3-dihydroxy-4-methoxyacetophenone to precipitate and collected by filtration.

The mother-liquid was stirred with water (2.67 L) and 27.7%-w/w NaOH (0.44 kg) for 30 minutes, allow to separate for 30 minutes. The aqueous phase was removed and the organic phase was stirred for 30 minutes a second time with fresh water (2.67 L) and 27.7%-w/w NaOH (0.44 kg), allowed to separate for 30 minutes before the aqueous phase was removed. The organic phase was concentrated as much as possible in vacuum applying 65° C. to 75° C. on the reactor mantle. When the distillation was slow, addition of EtOH (1.5 L) took place and the mixture was concentrated once more as much as possible in vacuum applying 65° C. to 75° C. on the reactor mantle.

When the distillation was slow, the resulting thick slurry was added EtOH (2 L) and heated to reflux which formed a clear solution. Slow addition of water (1.5 L) at a pace that allowed to maintain the reflux was followed by a slow cooling to 5° C. during 10 hours produced a suspension of title compound. The product was isolated by filtration and washed with a mixture of water (0.38 L) and EtOH (0.5 L) before the yellow solid material of title compound was dried in vacuum at 40° C. This produced title compound (0.44 kg, 1.57 mol) in 28% yield. $^1$H NMR (600 MHz, DMSO-d$_6$) δ 7.30 (d, J=9.0 Hz, 1H), 6.75 (d, J=9.0 Hz, 1H), 3.88 (s, 3H), 2.90-2.78 (m, 4H), 2.49 (s, 3H), 2.30-2.22 (m, 2H), 2.21-2.14 (m, 2H).

Steps (2a) and (2b): Preparation of 2-(3,5-dichloropyridine-4-yl)-1-(7-hydroxy-2',3',5',6'-tetrahydrospiro[1,3-benzodioxole-2,4'-(4H)-thiopyran]-4-yl)ethanone In a suitable reactor was placed 1-(7-methoxyspiro[1,3-benzodioxole-2,4'-tetrahydrothiopyran]-4-yl)ethanone (1.00 kg, 3.57 mol) and 3,4,5-trichloropyridine (1.04 kg, 5.70 mol) followed by addition of NMP (2.5 kg). The solution was stirred and cooled to −5° C. In a separate vessel was prepared a solution of tert-BuONa (1.03 kg, 10.7 mol) in NMP (2.5 kg) which was slowly pumped into the reactor while keeping the temperature below 15° C. during the addition.

After complete addition the reaction temperature was kept at 15° C. and the progression monitored by in-process control using HPLC. The reaction was considered complete when >98% of the 1-(7-methoxyspiro[1,3-benzodioxole-2,4'-tetrahydrothiopyran]-4-yl)ethanone was converted into 2-(3,5-dichloropyridine-4-yl)-1-(7-methoxy-2',3',5',6'-tetrahydro-spiro[1,3-benzodioxole-2,4'-(4H)-thiopyran]-4-yl)ethanone (not isolated intermediate), based on the ratio of HPLC %-area of 1-(7-methoxyspiro[1,3-benzodioxole-2,4'-tetrahydrothiopyran]-4-yl)ethanone and 2-(3,5-dichloropyridine-4-yl)-1-(7-methoxy-2',3',5',6'-tetrahydro-spiro[1,3-benzodioxole-2,4'-(4H)-thiopyran]-4-yl)ethanone. At this point the reaction mixture can be kept for up to 2 days at 5° C. if necessary.

To the reaction mixture was added 5-tert-butyl-2-methyl thiophenol (1.03 kg, 5.70 mol) and K$_2$CO$_3$ (0.54 kg, 3.92 mol) and the mixture was heated to 80° C. The reaction was considered complete when >85% of the 2-(3,5-Dichloropyridine-4-yl)-1-(7-methoxy-2',3',5',6'-tetrahydro-spiro[1,3-benzodioxole-2,4'-(4H)-thiopyran]-4-yl)ethanone was converted into the title compound, based on the ratio of HPLC %-area of 2-(3,5-Dichloropyridine-4-yl)-1-(7-methoxy-2',3',5',6'-tetrahydro-spiro[1,3-benzodioxole-2,4'-(4H)-thiopyran]-4-yl)ethanone and the title compound.

The reaction mixture was cooled to 20° C., added hexane (5 L), 27.7%-w/w NaOH (0.35 L) and water (5 L) followed by rapid stirring for 15 min to 30 min. After stopping the agitation and the phases had separated, the aqueous phase was kept while the organic phase was discarded. To the aqueous phase was added toluene (0.8 L) and hexane (4.2 L) followed by rapid stirring for 15 min to 30 min after which the agitation was stopped and the phases allowed to separate. The aqueous phase was kept and treated once more with toluene (2 L) and hexane (3 L) by rapid stirring for 15 min to 30 min, followed by stopping the agitation and allowing the phases to separate. The aqueous phase was kept and treated a third time with toluene (2.5 L) and hexane (2.5 L) by rapid stirring for 15 min to 30 min, followed by stopping the agitation and allowing the phases to separate.

The aqueous phase was returned to the reactor, added EtOAc (6 L), water (2 L) and slowly added AcOH (1.03 kg). Once the addition of AcOH was completed, stirring was continued for another 20 min to 30 min before agitation was stopped and the phases allowed to separate. The organic phase was transferred to a storage tank and kept, while the aqueous phase was returned to the reactor, added EtOAc (6 L), heated to 40° C. and stirred for 20 min to 30 min before agitation was stopped and the phases allowed to separate again. The aqueous phase was removed to waste and the organic phase on the storage tank was transferred to the reactor and combined.

The combined organic phases was added water (4 L) and stirred at 40° C. for 20 min to 30 min before agitation was stopped and the phases allowed to separate. The aqueous phase was removed and the organic phase once more added water (4 L) and NaCl (sat.) (4 L) followed by stirring at 40° C. for 20 min to 30 min before agitation was stopped and the phases allowed to separate. The aqueous phase was removed and the organic phase concentrated as much as possible by vacuum and heating at 50° C. to 60° C. When the distillation became slow addition of EtOAc (2 L) was followed by another concentration in vacuum to remove any water still present.

To the residue was added acetone (5.5 L) and the mixture was heated to reflux and complete dissolution was ensured. While the solution was refluxing, slow addition of hexane (12.5 L) took place such as reflux was maintained throughout the addition. Once the addition was completed the reaction mixture was cooled slowly to room temperature over a period of 5 hrs to 8 hrs and then further cooling to 0° C. over a period of another 5 hrs to 8 hrs.

The crude product was isolated by filtration, washed using a mixture of acetone (1 L) and hexane (2 L), dried in vacuum at 40° C. This produced the title compound (0.83 kg, 2.01 mol) as an off-white to yellowish solid in 56% yield. $^1$H NMR (600 MHz, DMSO-$d_6$) δ 10.76 (s, 1H), 8.65 (s, 2H), 7.26 (d, J=9.0 Hz, 1H), 6.56 (d, J=9.0 Hz, 1H), 4.59 (s, 2H), 2.97-2.89 (m, 2H), 2.86-2.79 (m, 2H), 2.39-2.31 (m, 2H), 2.23-2.15 (m, 2H).

Step (2c): Preparation of 2-(3,5-Dichloropyridine-4-yl)-1-(7-tetrabutylammonium oxido-2',3',5',6'-tetrahydro-spiro[1,3-benzodioxole-2,4'-(4H)-thiopyran]-4-yl)ethanone The crude 2-(3,5-Dichloropyridine-4-yl)-1-(7-hydroxy-2',3',5',6'-tetrahydro-spiro[1,3-benzodioxole-2,4'-(4H)-thiopyran]-4-yl)ethanone (0.83 kg, 2.01 mol) was transferred to the reactor, added THF (1.11 L) and stirred until dissolved before addition of aqueous N(Bu$_4$)$^+$OH$^-$ (1.83 kg) took place. The reaction mixture was heated to 45° C. and stirred for 1 hr to 2 hrs ensuring complete salt-formation. To the reactor was added MTBE (4.15 L), water (4.15 L) and NaCl (sat.) (1.25 L) under vigorously stirring for 1 hr to 2 hr followed by a slow cooling to 5° C. over a period of 1 hr to 4 hrs, causing the TBA-salt of 2-(3,5-Dichloropyridine-4-yl)-1-(7-hydroxy-2',3',5',6'-tetrahydro-spiro[1,3-benzodioxole-2,4'-(4H)-thiopyran]-4-yl)ethanone to precipitate. The agitation was stopped and the phases separated (three phases), where the aqueous phase was transferred carefully to waste while ensuring that the intermediate phase of the title compound was kept in the reactor. Once the separation was completed, addition of water (2.08 kg) was followed by heating to 35° C. while stirring vigorously for 1 hr to 2 hrs. The reaction mixture was slowly cooled to 5° C. over a period of 1 hr to 4 hrs, causing the TBA-salt of 2-(3,5-Dichloropyridine-4-yl)-1-(7-hydroxy-2',3',5',6'-tetrahydro-spiro[1,3-benzodioxole-2,4'-(4H)-thiopyran]-4-yl)ethanone to precipitate again and the agitation was stopped to allow the phases to separate. The aqueous phase was transferred carefully to waste as before and the remaining content holding the product was filtered and washed with MTBE (4.15 L) before dried in vacuum at 40° C. The title compound (1.26 kg, 1.93 mol) was isolated as an off-white solid in 55% yield overall. $^1$H NMR (600 MHz, DMSO-$d_6$) δ 8.58 (s, 2H), 6.98 (d, J=9.2 Hz, 1H), 5.76 (d, J=9.2 Hz, 1H), 4.39 (s, 2H), 3.24-3.08 (m, 8H), 2.91-2.82 (m, 2H), 2.82-2.74 (m, 2H), 2.23-2.13 (m, 211), 2.11-1.99 (m, 2H), 1.67-1.44 (m, 8H), 1.31 (h, =7.4 Hz, 8H), 0.93 (t, J=7.4 Hz, 12H).

Step (3): Preparation of 2-(3,5-dichloropyridine-4-yl)-1-(7-difluoromethoxy-2',3',5',6'-tetrahydro-spiro[1,3-benzodioxole-2,4'-(4H)-thiopyran]-4-yl)ethanone A reactor connected with at scrubber filled with DMF (approx. 5 L) was charged with 2-(3,5-dichloropyridine-4-yl)-1-(7-tetrabutylammonium oxido-2',3',5',6'-tetrahydro-spiro[1,3-benzodioxole-2,4'-(4H)-thiopyran]-4-yl)ethanone (1.0 kg, 1.53 mol) followed by addition of DMF (12 L) and stirred until complete dissolution at room temperature. The reactor was closed and the slow addition of chlorodifluoromethane (1.32 kg, 15.3 mol) was conducted such that the pressure never increased by more than 0.05 bar. Once the addition was completed, the reactor was re-opened allowing for ventilation through the scrubber and the temperature was increased to 65° C. in the reactor.

The progression of the reaction was monitored by in-process controls and analysed by HPLC every second hour. The reaction was considered complete when >93% of the 2-(3,5-dichloropyridine-4-yl)-1-(7-tetrabutylammonium oxido-2',3',5',6'-tetrahydro-spiro[1,3-benzodioxole-2,4'-(4H)-thiopyran]-4-yl)ethanone was converted into the title compound, based on the ratio of HPLC %-area of 2-(3,5-dichloropyridine-4-yl)-1-(7-tetrabutylammonium oxido-2',3',5',6'-tetrahydro-spiro[1,3-benzodioxole-2,4'-(4H)-thiopyran]-4-yl)ethanone and the title compound.

When the reaction was completed, water (1 L), 27.7%-w/w NaOH (50 mL) and MTBE (2 L) was added in that order and the mixture was stirred efficiently for 30 min to 45 min. At this point EtOAc (5 L) and more water (10 L) were added and the mixture stirred for another 30 min to 45 min before agitation was stopped and the phases were allowed to separate. The organic phase was kept in a storage tank and the aqueous phase returned to the reactor. To the reactor was added fresh MTBE (2 L), EtOAc (5 L) and the mixture stirred efficiently for 30 min to 45 min before agitation was stopped and the phases were allowed to separate. The organic phase was mixed with the previous organic phase in the storage tank and the aqueous phase returned to the reactor for a third extraction. To the reactor was added fresh MTBE (2 L), EtOAc (5 L) and the mixture stirred efficiently for 30 min to 45 min before agitation was stopped and the phases were allowed to separate.

The aqueous phase was discarded to waste, while the combined organic phases were returned to the reactor, added water (5 L) and stirred efficiently for 30 min to 45 min before agitation was stopped and the phases were allowed to separate. The aqueous phase was discarded to waste, and fresh water (5 L) was added followed by efficient stirring for 30 min to 45 min before agitation was stopped and the phases were allowed to separate. The aqueous phase was discarded to waste and the organic phase concentrated as much as possible using vacuum and heating to 50° C. to 60° C. When the distillation becomes slow, 2-PrOH (5 L) was added and the mixture heated to reflux while stirring ensures complete dissolution before water (1.7 L) was slowly added in a rate ensuring the temperature to be >75° C. After the addition was completed the mixture was slowly cooled to 5° C. over a period of 5 hrs to 12 hrs followed by another 3 hours stirring at 5° C. The precipitated product was isolated by filtration, washed with a mixture of water (2 L) and 2-PrOH (2 L), followed by a second washing using water (4 L). After drying in vacuum at 45° C. the title compound (0.65 kg, 1.40 mol) was isolated as off-white solid material in 92% yield. $^1$H NMR (600 MHz, DMSO-$d_6$) δ 8.67 (s, 2H), 7.40 (d, J=9.0 Hz, 1H), 7.39 (t, J=72.9 Hz, 1H), 6.93 (d, J=9.0 Hz, 1H), 4.68 (s, 2H), 2.98-2.89 (m, 2H), 2.88-2.80 (m, 2H), 2.43-2.36 (m, 2H), 2.30-2.18 (m, 2H).

Step (4): Preparation of 2-(3,5-dichloro-1-oxido-pyridine-4-yl)-1-(7-difluoromethoxy-2',3',5',6'-tetra-hydro-spiro[1,3-benzodioxole-2,4'-(4H)-thiopyran-1',1'-dioxide]-4-yl)ethanone A reactor was charged with acetic acid (3.8 kg), 2-(3,5-dichloropyridine-4-yl)-1-(7-difluoromethoxy-2',3',5',6'-tetrahydro-spiro[1,3-benzodioxole-2,4'-(4H)-thiopyran]-4-yl)ethanone (1 kg, 2.2 mol) and stirred shortly to ensure a homogeneous suspension. Peracetic acid (40% in acetic acid, 1.65 kg; 8.67 mol; 4 eq.) was added slowly over a period of hours (3-5 hrs), keeping the temperature between 25-40° C., to control the rise in temperature. The suspension becomes homogeneous during the addition.

The mixture was heated to 50° C. and stirred for 14-18 hr. The reaction mixture was sampled (IPC, conversion: >99%=completed). "The reaction mixture was cooled to 25° C., and a solution of Na2S2O5 (0.42 kg, 2.21 mol) in water (2.7 kg) was slowly added while keeping the temperature below 35° C. Once the addition was completed the resulting mixture was stirred for another 10-20 minutes before tested negative for residue peroxides. Addition of IPA (5.0 L) took place and heating to 60° C. forming a homogenous mixture which was blank-filtered. To the filtered solution was added water (15 kg) at a rate maintaining a temperature between 55-60° C. The reaction mixture was stirred at 60° C. for another 30-60 minutes before cooling to 5° C. with a cooling ramp of 5° C./hr. The suspension was stirred another 2 hours at 5° C. before filtering of the product.

The crystals was filtered and washed with water (1.7 kg). The wet cake was returned to the reactor and dissolved completely in EtOH (20.4 kg) when heated to reflux. The clear solution was cooled to 70° C., seeded (10 grams of the title compound from previous batch) and then cooled to 5° C. with a cooling ramp of 5° C./hr. The suspension was stirred at 5° C. not less than 2 hours.

The product was isolated by filtration, washed with EtOH/water (2.0 kg EtOH and 0.25 kg water), and dried under vacuum (45° C., p<10 mbar). The yield of the title compound was 0.8 kg (75%), with a purity of 98.5%-area on HPLC. $^1$H NMR (600 MHz, CDCl$_3$) δ 8.24 (s, 2H), 7.52 (d, J=9.0 Hz, 1H), 6.89 (d, J=9.0 Hz, 1H), 6.70 (t, J=72.3 Hz, 1H), 4.49 (s, 2H), 3.47-3.39 (m, 2H), 3.32-3.24 (m, 2H), 2.83-2.76 (m, 2H), 2.75-2.68 (m, 2H).

CLAUSES

In view of the description the present inventors have in particular provided:

Clause 1. A method for the preparation of a compound of formula (I)

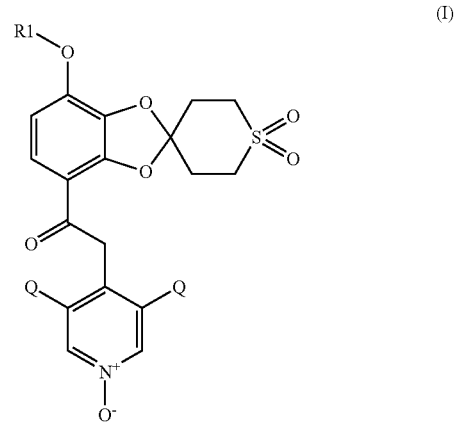

wherein $R_1$ is selected from $CHF_2$ and $CF_3$, Q is selected from chloro, bromo and fluoro, comprising one or more of the following steps:
(1) reacting a compound of formula (II)

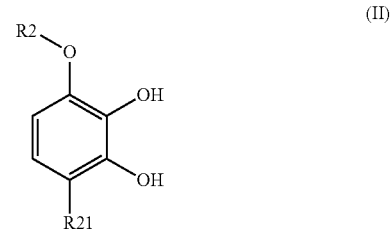

wherein $R_2$ is selected from hydrogen, $C_{1-6}$-alkyl and arylalkyl, $R_{21}$ is selected from hydrogen, $C(O)R_{22}$ and $C(O)OR_{22}$, and $R_{22}$ is selected from hydrogen and $C_{1-6}$-alkyl; with a compound of formula (III)

wherein ">—<" represents a single bond, a double bond or two single bonds, and when ">—<" represents a double bond or two single bonds, "═" is a single bond, and when ">—<" represents a single bond, "═" is a double bond, $R_3$ represents oxygen when ">—<" represents a double bond and $R_3$ represents O—$C_{1-6}$-alkyl when ">—<" represents a single bond or two single bonds In the presence of an acid catalyst to form a compound of formula (IV)

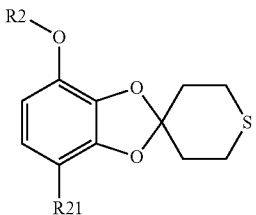

(IV)

wherein $R_2$ and $R_{21}$ are as defined above;

(2a) reacting the resulting compound of formula (IV) with a pyridine compound of formula (V)

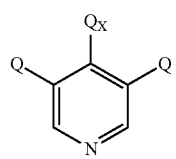

(V)

wherein Q is as defined above and $Q_x$ is selected from chloro, bromo, fluoro and iodo to form an intermediate compound of formula (VI)

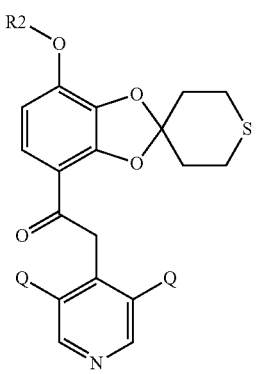

(VI)

wherein $R_2$ and Q are as defined above;

(2b) reacting the compound of formula (VI) with a compound of formula (VII)

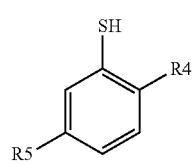

(VII)

wherein $R_4$ and $R_5$ represent $C_{1-6}$-alkyl, to form a compound of formula (VIII)

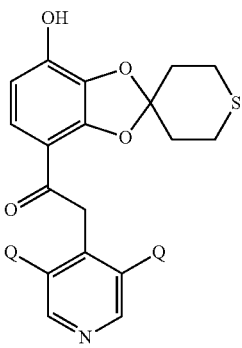

(VIII)

wherein Q is defined above;

(2c) reacting the compound of formula (VIII) with aqueous $N(Bu_4)^+OH^-$ to form a compound of formula (IX)

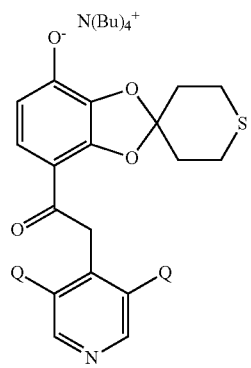

(IX)

wherein Q is as defined above; followed by (3) alkylating the resulting compound of formula (IX) by reacting with a hydrochlorofluorocarbon compound, $R_1$—Cl, wherein $R_1$ is as defined above, to form a compound of formula (XI)

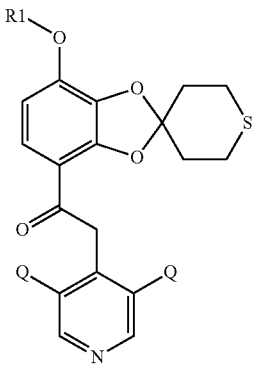

(XI)

wherein $R_1$ and Q are as defined above; and (4) oxidating the resulting compound of formula (XI) to prepare the compound of formula (I) wherein $R_1$ and Q are as defined above.

Clause 2. The method according to clause 1 wherein the in step (1), the acid catalyst is in form of a silicate mineral selected from Montmorillonite K10, Montmorillonite K30, Zeolite HSZ-350HUA and Zeolite HSZ-360HUA.

Clause 3. The method according to clause 2 wherein the silicate mineral is Montmorillonite K10.

Clause 4. The method according to any one of the preceding clauses wherein step (1) is conducted in a solvent selected from toluene, benzene, 2-methyl-THF, EtOAc, heptane or dichlorobenzene.

Clause 5. The method according to clause 4 wherein the solvent is toluene.

Clause 6. The method according to any one of the preceding clauses wherein in step (2a) the coupling is conducted in an aprotic polar solvent, e.g. selected from NMP, DMF, DMI, DMSO, EtOAc, MeCN and THF, and mixtures hereof, in the presence of a base, e.g. selected from tert-BuONa, tert-BuOK, $K_2CO_3$, $Na_2CO_3$, $KHCO_3$, $NaHCO_3$, $Et_3N$ and DIPEA.

Clause 7. The method according to clause 6 wherein the aprotic polar solvent is NMP, and the base is tert-BuONa.

Clause 8. The method according to any one of the preceding clauses wherein the deprotection in step (2b) is conducted in a solvent e.g. selected from NMP, DMSO, DMF, and mixtures hereof, in the presence of a base, e.g. selected from $K_2CO_3$, $Na_2CO_3$, $KHCO_3$, $NaHCO_3$, $CsCO_3$, TEA and DIPEA.

Clause 9. The method according to clause 8 wherein the solvent is NMP and the base is $K_2CO_3$.

Clause 10. The method according to any one of the preceding clauses wherein step (2c) is conducted in the presence of THF, toluene or EtOAc.

Clause 11. The method according to clause 10 wherein the solvent is THF.

Clause 12. The method according to any one of the preceding clauses wherein the reaction in step (3) is conducted using a hydrochlorofluorocarbon $R_1$-Cl compound in the presence of a in an aprotic polar solvent, e.g. selected from DMF, NMP, DMI, DMSO, EtOAc and THF.

Clause 13. The method according to clause 12 wherein the reaction is conducted using chlorodifluoromethane in DMF.

Clause 14. The method according to any one of the preceding clauses wherein the reaction in step (4) is conducted in the presence of peracetic acid in acetic acid or $H_2O_2$ (aq) in formic acid or acetic acid.

Clause 15. The method according to clause 14 wherein the reaction is conducted using peracetic acid in acetic acid.

Clause 16. The method according to any one of the preceding clauses wherein $R_1$ is $CHF_2$.

Clause 17. The method according to any one of the preceding clauses wherein all of Q and $Q_x$ are chloro.

Clause 18. An intermediate compound of formula (IV)

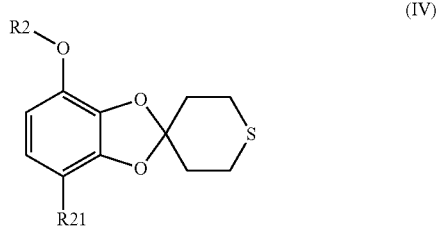

(IV)

wherein $R_2$ is selected from hydrogen, $C_{1-6}$-alkyl and arylalkyl, $R_{21}$ is selected from hydrogen, $C(O)R_{22}$ and $C(O)OR_{22}$, and $R_{22}$ is selected from hydrogen and $C_{1-6}$-alkyl.

Clause 19. The intermediate compound according to clause 18 which is 1-(7-methoxyspiro[1,3-benzodioxole-2,4'-tetrahydrothiopyran]-4-yl)ethanone.

Clause 20. An intermediate compound of formula (IX)

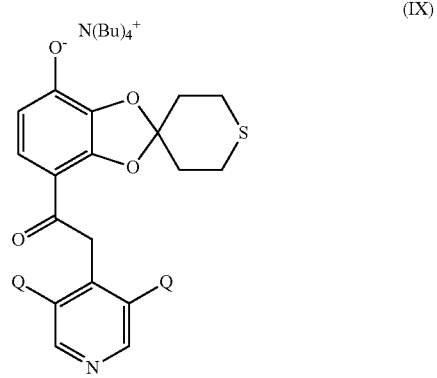

(IX)

wherein Q is selected from chloro, bromo and fluoro.

Clause 21. The intermediate compound according to clause 20 which is 2-(3,5-dichloropyridine-4-yl)-1-(7-tetrabutylamminium oxido-2',3',5',6'-tetrahydro-spiro[1,3-benzodioxole-2,4'-(4H)-thiopyran]-4-yl)ethanone.

Clause 22. A method for preparing a compound of formula (IV)

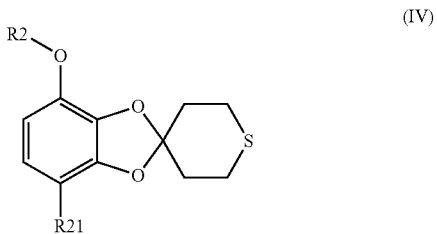

(IV)

wherein $R_2$ is selected from hydrogen, $C_{1-6}$-alkyl and arylalkyl, $R_{21}$ is selected from hydrogen, $C(O)R_{22}$ and $C(O)OR_{22}$, and $R_{22}$ is selected from hydrogen and $C_{1-6}$alkyl; comprising step (1) as defined in clause 1.

Clause 23. A method for preparing a compound of formula (IX)

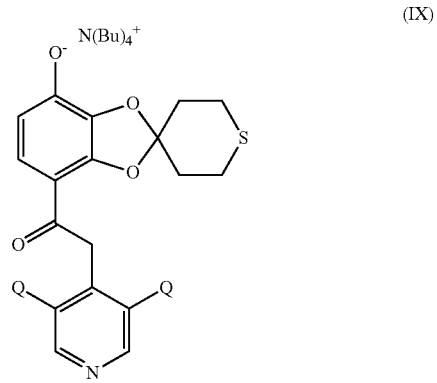

(IX)

wherein Q is selected from chloro, bromo and fluoro, comprising step (2a), (2b) and (2c) as defined in clause 1.

Clause 24. A method for preparing a compound of formula (IX)

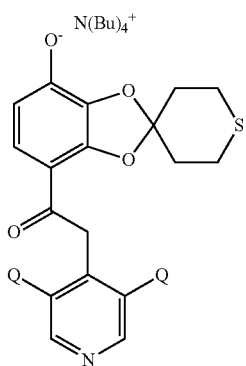
(IX)

wherein Q is selected from chloro, bromo and fluoro, comprising step (1), (2a), (2b) and (2c) as defined in clause 1.

Clause 25. A method for preparing a compound of formula (I)

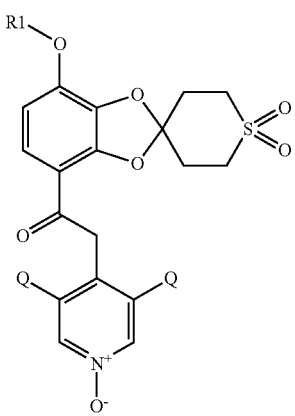
(I)

wherein $R_1$ is selected from $CHF_2$ and $CF_3$, and Q is selected from chloro, bromo and fluoro, comprising each of the steps (1), (2a), (2b) and (2c) as defined in clause 1, followed by alkylating and subsequently oxidation of the resulting compound.

Clause 26. A method for preparing a compound of formula (I)

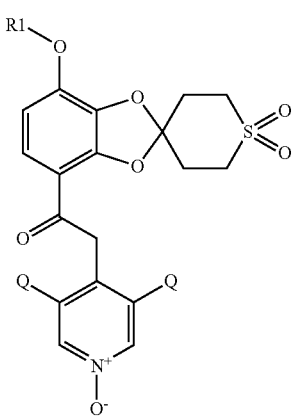
(I)

wherein $R_1$ is selected from $CHF_2$ and $CF_3$, and Q is selected from chloro, bromo and fluoro, comprising each of the steps (1), (2a), (2b) and (2c), (3) and (4) as defined in clause 1.

Clause 27. A compound of formula (I)

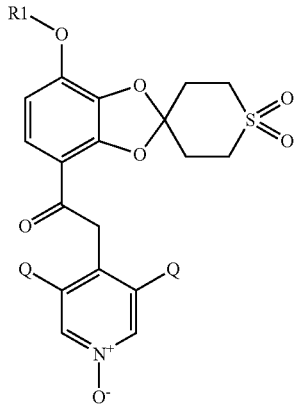
(I)

wherein $R_1$ is selected from $CHF_2$ and $CF_3$, and Q is selected from chloro, bromo and fluoro, obtained by method of clause 1.

Clause 28. A compound of formula (I)

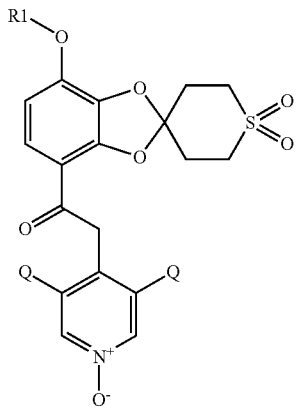
(I)

wherein $R_1$ is selected from $CHF_2$ and $CF_3$, and Q is selected from chloro, bromo and fluoro, made by the steps (1), (2a), (2b) and (2c) as defined in clause 1, followed by alkylating and subsequently oxidation of the resulting compound.

The invention claimed is:

1. A method for the preparation of a compound of formula (I)

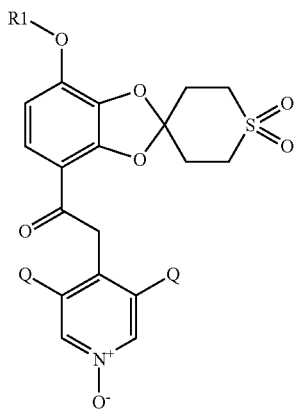
(I)

wherein R₁ is selected from CHF₂ and CF₃, Q is selected from chloro, bromo and fluoro, comprising each of the steps:

(1) reacting a compound of formula (II)

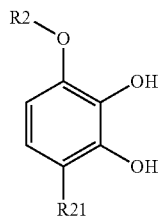
(II)

wherein R₂ is selected from hydrogen, C₁₋₆-alkyl and arylalkyl, R₂₁ is C(O)CH₃; with a compound of formula (III)

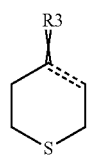
(III)

wherein "$\bowtie$" represents a single bond, a double bond or two single bonds, and when "$\bowtie$" represents a double bond or two single bonds, "═" is a single bond, and when "$\bowtie$" represents a single bond, "═" is a double bond, R₃ represents oxygen when "$\bowtie$" represents a double bond and R₃ represents O—C₁₋₆-alkyl when "$\bowtie$" represents a single bond or two single bonds in the presence of an acid catalyst to form a compound of formula (IV)

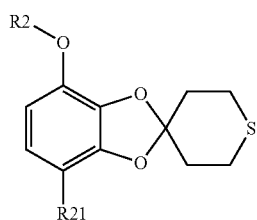
(IV)

wherein R₂ and R₂₁ are as defined above;

(2a) reacting the resulting compound of formula (IV) with a pyridine compound of formula (V)

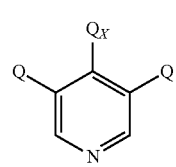
(V)

wherein Q is as defined above and Q$_X$ is selected from chloro, bromo, fluoro and iodo to form an intermediate compound of formula (VI)

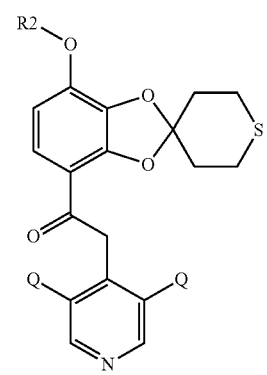
(VI)

wherein R₂ and Q are as defined above;

(2b) reacting the compound of formula (VI) wherein R₂ is selected from C₁₋₆-alkyl and arylakyl with a compound of formula (VII)

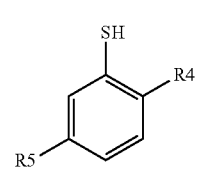
(VII)

wherein R₄ and R₅ represent C₁₋₆-alkyl, to form a compound of formula (VIII)

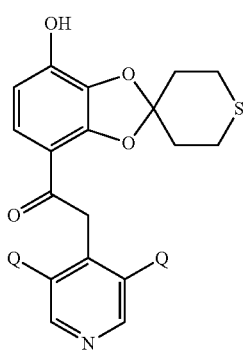
(VIII)

wherein Q is defined above;

(2c) reacting the compound of formula (VIII) with aqueous N(Bu₄)⁺OH⁻ to form a compound of formula (IX)

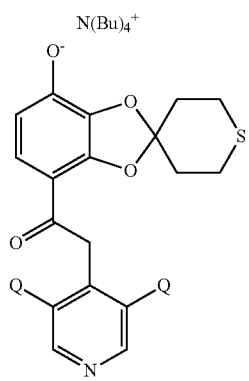

(IX)

wherein Q is as defined above; followed by alkylating and subsequent oxidation of the resulting compound to prepare the compound of formula (I) wherein R1 and Q are as defined above.

2. The method according to claim 1 wherein in step (1), the acid catalyst is in form of the silicate mineral Montmorillonite K10.

3. The method according to claim 1 wherein in step (2a) is conducted in an aprotic polar solvent in the presence of a base.

4. The method according to claim 1 wherein step (2b) is conducted in a solvent selected from NMP, DMSO, DMF and mixtures thereof, in the presence of a base.

5. The method according to claim 1 wherein $R_1$ is $CHF_2$.

6. The method according to claim 1 wherein all of Q and $Q_x$ are chloro.

7. The method according to claim 1, wherein the alkylating and subsequent oxidation steps comprise alkylating the compound of formula (IX) by reacting with a hydrochlorofluorocarbon compound, $R_1$-Cl, wherein $R_1$ is as defined in claim 1, to form a compound of formula (XI)

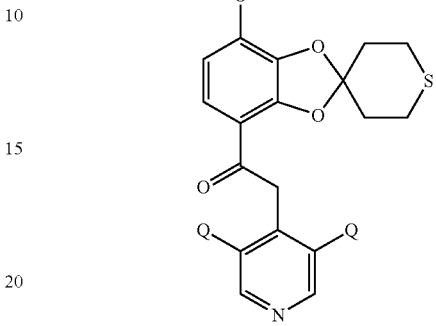

(XI)

wherein $R_1$ and Q are as defined in claim 1; and oxidation of the compound of formula (XI) to prepare the compound of formula (I) wherein $R_1$ and Q are as defined in claim 1.

8. The method according to claim 7 wherein alkylating the compound of formula (IX) is conducted using a hydrochlorofluorocarbon in the presence of an aprotic polar solvent.

9. The method according to claim 7 wherein the oxidation of the compound of formula (XI) is conducted using peracetic acid in acetic acid.

* * * * *